United States Patent
Ryu et al.

(10) Patent No.: US 7,288,668 B2
(45) Date of Patent: Oct. 30, 2007

(54) PROCESS FOR MAKING DIARYL CARBONATE

(75) Inventors: J. Yong Ryu, League City, TX (US); Abraham P. Gelbein, Raleigh, NC (US)

(73) Assignee: Catalytic Distillation Technologies, Pasadena, TX (US)

( * ) Notice: Subject to any disclaimer, the term of this patent is extended or adjusted under 35 U.S.C. 154(b) by 190 days.

(21) Appl. No.: 11/281,823

(22) Filed: Nov. 17, 2005

(65) Prior Publication Data

US 2007/0112214 A1 May 17, 2007

(51) Int. Cl.
*C07C 69/96* (2006.01)

(52) U.S. Cl. ..................................... 558/274

(58) Field of Classification Search ................. 558/274
See application file for complete search history.

(56) References Cited

U.S. PATENT DOCUMENTS

| | | |
|---|---|---|
| 5,177,290 A | 1/1993 | Ryu et al. |
| 5,210,268 A | 5/1993 | Fukuoka et al. |
| 5,218,135 A | 6/1993 | Buysch et al. |
| 5,344,954 A | 9/1994 | Schon et al. |
| 5,362,901 A | 11/1994 | Wagner et al. |
| 5,426,207 A | 6/1995 | Harrison et al. |
| 5,463,102 A | 10/1995 | Schon et al. |
| 5,523,451 A | 6/1996 | Rechner et al. |
| 5,565,605 A | 10/1996 | Tsuneki et al. |
| 6,262,210 B1 | 7/2001 | Tojo et al. |
| 6,392,078 B1 | 5/2002 | Ryu et al. |
| 6,767,517 B2 | 7/2004 | de Bruin et al. |

*Primary Examiner*—Kamal A. Saeed
(74) *Attorney, Agent, or Firm*—Osha Liang LLP

(57) ABSTRACT

Diphenyl carbonate is produced by reacting phenol with diethyl carbonate in a series of fixed bed reactors each of which is connected at different position on a distillation column via side draw and return streams. The composition of material in a distillation column varies along the length of the column, which is predictable under a given set of conditions of temperature and pressure, thus withdrawing streams at different stages in the column, allows the reactor receiving the feed from a particular stage to be operated under conditions to maximize the desired reaction, while allowing the unreacted or byproduct to go back into the distillation and be sent to a stage (by the equilibrium of the distillation) where they are favorably treated in a reactor.

13 Claims, 1 Drawing Sheet

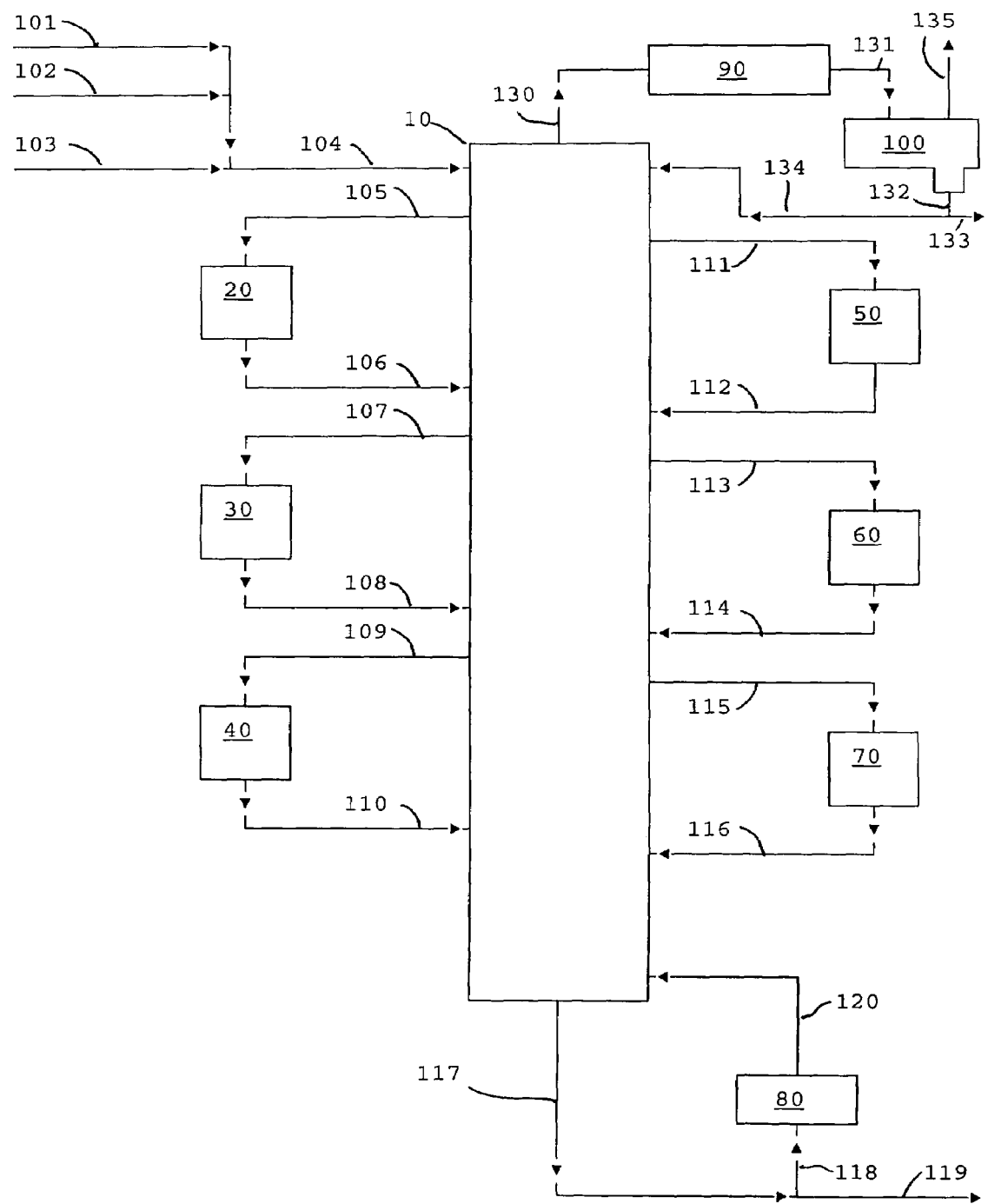

PROCESS FOR MAKING DIARYL CARBONATE

BACKGROUND OF THE INVENTION

1. Field of the Invention

The present invention relates to a process for the production of diaryl carbonates, such as diphenyl carbonate. More particularly, the invention relates to a process for the production of diaryl carbonates wherein a series of fixed bed reactors withdraw feed from a single distillation column at different separation stages and return the product to the column. The reactors may be operated at different conditions than those of the distillation column to optimize production of diaryl carbonates.

2. Related Art

Diphenyl carbonate is a valuable intermediate for the production of polycarbonate. In current commercial practice, diphenyl carbonate is produced by transesterification with an alcohol followed by disproportionation using dimethyl carbonate (DMC) and phenol. Such processes are disclosed in U.S. Pat. Nos. 5,210,268; 6,197,918; and 6,262,210. The typical reaction is:

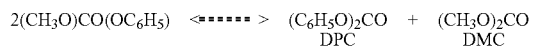

The unconverted dimethyl carbonate is recovered as a mixture with the coproduct methanol. Dimethyl carbonate is separated from the mixture and recycled. However, dimethyl carbonate and methanol form an azeotrope. Therefore, the recovery of dimethyl carbonate in the mixture involves breaking the azeotropic mixture which is energy consuming and expensive.

Heretofore higher conversions to alkyl phenyl carbonate and thence to diphenyl carbonate have been achieved by carrying out the reaction in two steps each of which involves continuous removal of the lighter components from the reacting mixtures. In the first step the alkyl alcohol is the lighter component, and in the second step dialkyl carbonate is the lighter component. This has normally been achieved by some form of reactive distillation wherein the reaction in the presence of the catalyst is carried out with simultaneous separation of components by distillation. Such processes can be efficient provided the reaction rates are adequate in the temperature range set by the vapor-liquid equilibria of the distilling system. Pressure and reflux ratio can be adjusted to effect the reaction zone temperature profile and/or reaction volume can be increased but such changes can increase the cost of the process.

U.S. Pat. No. 6,093,842 addressed this problem by using reactive distillation and an entraining agent that did not form an azeotrope with the dialkyl carbonate or the alkyl alcohol. The patentee states, "While the dialkyl carbonate used as a starting material in the method of the invention may in theory be any dialkyl carbonate, it will be appreciated that in practice it will be preferred to use a dialkyl carbonate with a small alkyl group, such as, for example dimethyl carbonate." However, the methanol is the cause of the azeotrope problem and the solution merely changes the manner of breaking the azeotrope. Also producing the dimethyl carbonate in the first place involves the same problem, i.e., breaking the azeotropic mixture to separate the product, dimethyl carbonate, from the product stream.

The present invention avoids the formation of azeotropes in the transesterification process.

SUMMARY OF THE INVENTION

Briefly the present invention is a process of preparing diaryl carbonates by reacting aromatic hydroxy compound with dialkyl carbonate in a series of fixed bed reactors each of which is connected at different positions on a distillation column via side-draw and return streams comprising the step of feeding aromatic hydroxy and dialkyl carbonate to a distillation zone having a plurality of stages, withdrawing liquid comprising aromatic hydroxy and dialkyl carbonate from a first stage to a first reaction zone to contact the liquid with a transesterification catalyst under conditions conducive to transesterification, returning a product from the first reaction zone to the distillation zone, withdrawing liquid comprising aryl alkyl carbonate from a second stage to a second reaction zone to contact the liquid with a disproportation catalyst under conditions conducive to disproportation, returning a product from the second reaction zone to the distillation zone, and separating diaryl carbonate as bottoms and alkyl alcohol as overheads. The reactors generally operate at different conditions of temperature and pressure than exist in the distillation column so that pumps and heat exchangers may be present in the reactor to distillation circulation loops. The distillation column contains separation stages above the last reactor in the series and below the first reactor in the series. Phenol in stoichiometric excess and dialkyl carbonate are fed to the inlet side of the reactor piped to the uppermost distillation column side-draw stream. Sufficient reaction and separation stages are provided such that essentially 100% conversion of the dialkyl carbonate is obtained with essentially alcohol produced as distillate product and essentially diphenyl carbonate together with the excess phenol produced as bottoms product. The catalysts used in the sidedraw reactors are preferably those which are suitable for both transesterification and disproportations. Thus, as the draw streams are taken along the distillation column, the streams withdrawn toward the lower part of the column contain a changing composition which are conducive of the disproportionation reaction, whereas the composition of the sidedraw streams in the upper portion of the distillation column is conducive of the transesterification. In a corresponding manner the reaction zones along the column shift from transesterification to disproportionation progressively down the column as the composition of the diphenyl carbonate increases.

Since the composition of material in a distillation column varies along the length of the column, which is predictable under a given set of conditions of temperature and pressure, withdrawing streams at different stages in the column, allows the reactor receiving the feed from a particular stage to be operated under conditions to maximize the desired reaction, while allowing the unreacted feed, intermediate product or byproduct to go back into the distillation and be sent to a stage (by the equilibrium of the distillation) where they are favorably treated in a reactor.

Preferred solid catalysts are mixed oxide catalysts composed of two to four different elements from Group IV, V and VI of the Periodic Table, preferably Ti, Zr, Hf, Nb, Ta, Mo, V, Bi and Si supported on porous materials such as silica, which have surface hydroxyl groups. Supported metal alkoxide or mixed metal alkoxide catalysts of the Group IV and V metal alkoxides, such as titanium alkoxides, zirconium alkoxides, vanadium alkoxides, niobium alkoxides, VO(OR)$_3$ or oligomers of oxoalkoxide, and the like constitute a preferred catalyst group. The transesterification catalyst and the disproportionation catalyst utilized in the present process may be the same or different.

BRIEF DESCRIPTION OF THE DRAWING

The FIGURE is a simplified flow diagram of the preferred embodiment of the invention.

DETAILED DESCRIPTION OF THE PREFERRED EMBODIMENT

Diphenyl carbonate is produced in a two step reaction wherein phenol first reacts with diethyl carbonate in the presence of a transesterification catalyst to produce ethyl phenyl carbonate and ethanol (1). This is followed by a second step disproportionation reaction wherein ethyl phenyl carbonate is converted to diphenyl carbonate and diethyl carbonate(2). The net reaction products are diphenyl carbonate and ethanol.

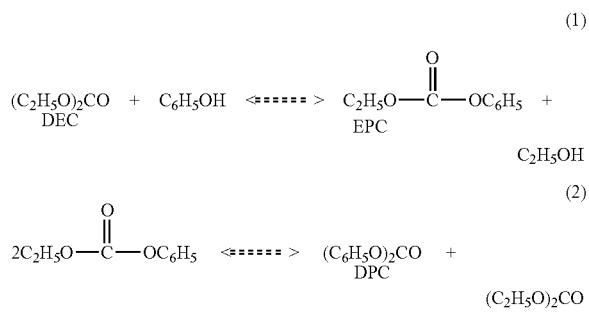

Typically the equilibrium constant for the first reaction is substantially less than one while that for the second reaction is somewhat greater than one. The first step can be carried out with equimolar amounts of phenol and diethyl carbonate or with and excess of either. In all cases the conversion of ethyl phenyl carbonate and diphenyl carbonate are impractically low, from the perspective of product recovery, at equilibrium.

Examples of organic carbonates produced by this invention are DPC (diphenyl carbonate), EPC (ethyl phenyl carbonate), MPC (methyl phenyl carbonate), DEC (diethyl carbonate), DMC (dimethyl carbonate), bis-(2-ethylhexyl) carbonate, and fatty acid mono-glyceride carbonates. The present invention is particularly useful in producing diphenyl carbonate (DPC) from DEC and phenol. Although DEC is the preferred dialkyl carbonate for the production of DPC, it is understood that the process is also useful for the production of DPC by using DMC or any other alkyl carbonate or alkyl aryl carbonate.

In a preferred embodiment the process of the production of diaryl carbonate comprises:

(a) distillation zone having an upper end, a lower end and a plurality of distillation stages arrayed along said distillation zone;

(b) a plurality of reaction zones arrayed along said distillation zone and associated with different distillation stages;

(c) supplying dialkyl carbonate and an aromatic hydroxy compound to said distillation zone;

(c) withdrawing a stream comprising dialkyl carbonate and an aromatic hydroxy compound from a first distillation stage to a first reaction zone;

(d) maintaining said first reaction zone under reaction conditions conducive for the transesterification of dialkyl carbonate and an aromatic hydroxy compound to produce alkyl aryl carbonate;

(e) transesterifing the dialkyl carbonate with the aromatic hydroxy compound in the presence of a catalyst to form alkyl aryl carbonate;

(f) returning a product stream from said first reaction zone to said distillation zone;

(g) withdrawing a stream comprising alkyl aryl carbonate and an aromatic hydroxy compound from a second distillation stage to a second reaction zone;

(h) maintaining the second reaction zone under reaction conditions conducive for the disproportionation of alkyl aryl carbonate to dialkyl carbonate;

(i) disproportionating the alkyl aryl carbonate in the presence of a catalyst to produce diaryl carbonate;

(j) returning a product stream from said secondary reaction zone to said distillation zone;

(k) removing vaporous alkyl alcohol and liquid diaryl carbonate from the distillation zone.

The catalyst in the reactors may be homogeneous or heterogenous, however the homogenous catalyst are difficult to separate from the reaction product and need to be recovered, recycled and make up added, which adds a separate cycle to the process. Heterogenous catalyst are preferred. Suitable solid transesterification and disproportionation catalysts capable of catalyzing the reactions described above are known and include metal alkoxide catalyst supported on a porous support such as silica.

The preferred heterogeneous catalysts are supported mixed oxides, hydroxides, oxyhydroxides and alkoxides of Group IV, V and VI elements which are deposited on porous supports. The mixed oxide catalysts may be combinations of two, three or four elements chosen from Mo, Nb, Ti, V Zr, Bi, and Si. These element are deposited in oxide or hydroxide or oxyhydroxide forms on a porous support such as silica, zirconia, and titania. Supports can be pellets, granules, extrudates, spheres, and the like in sizes of from about 1 to about 5 mm. The deposition can be carried out in a single step or multiple steps. The examples of the mixed oxide catalysts are $Nb_2O_3$—$TiO_2$, $V_2O_3$—$TiO_2$, $MoO_3$—$TiO_2$, $TiO_2$—$ZrO_2$, $Nb_2O_5$—$V_2O_3$, $MoO_3$—$V_2O_5$, $MoO_3$—$ZrO_2$, $TiO_2$—$ZrO_2$—$SiO_2$, $TiO_2$—$Nb_2O_5$—$SiO_2$, $MoO_3$—Nb $O_5$—$TiO_2$, $V_2O_5$—$Nb_2O_5$—$TiO_2$, $MoO_3$—$Nb_2O_5$—$SiO_2$, $TiO_2$—$Bi_2O_3$—$SiO$, $MoO_3$—$NbO_5$—$ZrO_2$, $TiO_2$—$Nb_2O_5$—$Bi_2O3$, $MoO_3$—$V_2Os$—$TiO_2$, $TiO_2$—$Bi_2O_3$—$SiO_2$, $MoO_3$—$Bi_2O_3$—$SiO_2$, $TiO_2$—$ZrO_2$—$Bi_2O_3$—$SiO_2$, and $TiO_2$—$ZrO_2$—$Nb_2O_5$—$Bi_2O_3$—$SiO_2$.

The general procedure for preparing these mixed oxide catalysts are impregnation and co-precipitation or a combination of these two, which are performed in a single step or multiple steps. One may perform impregnation of one, two or three metal components on a porous support or on a mixed oxide support prepared by co-precipitation. Impregnation can be performed in one step or multiple steps.

Co-precipitation products and impregnation products obtained in powdery forms are subjected to suitable heat treatment at temperatures from about 150° to about 600° C. The powdery materials are shaped in a suitable size of from about 1 to 5 mm for the fixed bed reactor. The shaped materials are calcined at temperature from 200° to about 750° C., preferably from about 250° to about 600° C. in air. Optionally one or two metal components can be deposited on a shaped material prepared by a co-precipitation or impregnation method in either powder form or shaped form and then calcined at from 200° to about 750° C., preferably from about 250° to about 600° C. in air. The co-precipitation and impregnation can be carried out in aqueous phase or in organic phase, such as hydrocarbons, ethers, ketones, alcohols, and mixtures of these.

When precipitation is carried out in organic phase, organometallic compounds are preferably used. For example, two different solutions of different organometallic compounds are added to a suitable organic solvent simultaneously with vigorous stirring under precipitation conditions at suitable temperatures. Sometimes a third solution is necessary during the addition or afterward to cause gelation or precipitation. An example of the third solution is water, basic or acidic water solution in a suitable organic solvent such as alcohol, ether, ketone, organic ester, or mixtures of these. Another optional method is simultaneously adding first organometallic solution and third solution to second organometallic solution with vigorous stirring. If necessary, the precipitates are aged at a suitable temperature form about 25° to about 200° C. for from 30 minutes to about 30 hours in suitable medium. Sometimes a coprecipitated product in aqueous medium is aged in neutral, mildly acidic or basic organic medium.

The aging medium may or may not contain a minor amount of water depending on the nature of the material to be aged. The aging medium could be mildly acidic, mildly basic or neutral. The aged product is dried at a temperature from about 100° to about 400° C. and then calcined at a temperature from about 250° to about 750° C. If necessary, impregnation of one or two elements on a suitable support is carried out by using an organic solution containing one or two organometallic compounds or aqueous solution containing one or two compounds. Optionally one can perform multiple impregnations by using different solutions.

However, one may choose to use any heterogeneous catalyst disclosed in the prior art, as long as the catalyst is suitable for a fixed bed reactor for the operation of a large commercial reactor. Examples of heterogenous catalysts disclosed in the prior art are titanium oxide, TS-1, Ti-MCM-41, molybdenum oxide, vanadium oxide, niobium oxide, lead oxide, and MgLa mixed oxide as appropriate and preferably supported as described herein.

It is important that a support should have surface hydroxyl groups. Silica is a preferred support. The term "treated support" or "treated silica" is understood to mean a support having an optimized population of surface hydroxyl groups for a given surface area for the preparation of the catalysts described herein. Depending on how silica is prepared, silica may not have a sufficient number of surface hydroxyl groups in a given surface area. For such a silica, the silica is treated to introduce extra surface hydroxyl groups with an aqueous base solution and then washed thoroughly with water, followed by calcination at a temperature from 280° to 650° C., prior to use. Optionally one may attempt to rehydrate a commercially available silica support. The rehydrated silica is calcined at a temperature from 280° to 650° C. to optimize the population density of surface hydroxyl groups prior to use. Therefore, the preferred silica support used for the preparation of a solid catalyst is "treated silica". A class of preferred supports, particularly silica supports are those that have had the surface hydroxyl groups increased by treatment with a base solution as describe to obtain the maximum number of hydroxyl groups without degrading the physical integrity and strength of the support. Controlling the sodium content on silica support is very important for the preparation of aromatic carbonates such as EPC and DPC, because basic impurities such as alkali metal oxide on silica causes unwanted side reactions and tends to cause catalyst instability. Alkali metal on silica support causes instability of the catalyst performance and undesired side reactions for the transesterification and disproportionation, which produces alkyl aryl carbonate and diary carbonate. The preferred "treated silica" support will have less than about 0.05 wt % Na, preferably less than about 0.03 wt % Na. Treating silica with aqueous alkali metal solution has an additional benefit of widening the pores. However, leaching out too much silica from silica support during the treatment with alkali metal solution can cause the problem of maintaining physical integrity and strength.

Other suitable catalysts are supported metal alkoxide or mixed metal alkoxide catalysts, which are prepared by bonding metal alkoxides to porous supporting materials through oxygen bridge bonds. The porous supporting materials must have surface hydroxyl groups, which react with alkoxy groups for the formation of oxygen bridge bonds. The preferred support is treated silica, which has less than about 0.05 wt % Na, preferably less than about 0.03 wt % Na. Optimizing the population of the surface hydroxyl groups on silica support is very important to create stable, strongly anchored metal alkoxide active sites, since no high temperature calcinations is involved to link active metal atoms to the surface of silica via M—O—Si bridge bonds. Maximizing the number of M—O—Si bridge bonds is highly desirable.

Thus, an optimized population of hydroxyl groups for a given surface includes the maximum number of hydroxy groups that can be obtained for the given surface area within the constraints of alkali metal content and support strength as described above.

The preferred metal alkoxides are Group IV and V metal alkoxides such as titanium alkoxides, zirconium alkoxides, vanadium alkoxides, niobium alkoxides, and the like. The Group V metal alkoxides include a lower valent alkoxide such as tetra-alkoxide and an oxytrialkoxide such as $VO(OR)_3$, or oligomers of oxoalkoxide. Examples of preferred supports are silica, zirconia, titania, titania-silica, silica-alumina, and silica-zirconia. Using treated silica is especially important for the preparation of supported metal alkoxide catalysts. An alkoxide catalyst on a support can have one or two different metal alkoxides.

The heterogeneous metal alkoxide catalysts are prepared by contacting a metal alkoxide solution or a mixed solution of two different metal alkoxides with a support such as silica at temperature from about 20° to about 400° F., preferably from about 40° to about 300° F. The alkoxide solution is prepared by dissolving one or two different metal alkoxides in a solvent. The solvent must not interfere with the oxygen bridge forming reaction in any way. Examples of such solvents are hydrocarbons, ethers, ketones, alcohols and mixtures thereof. When two different metal alkoxides are supported on a support, optionally two different metal alkoxide solutions are prepared and are reacted with a support in sequence.

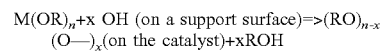

Where n=4 or 5, x=1, 2, 3 or 4 and R=alkyl or aryl group

Supported titanium alkoxide is an acidic catalyst. The higher activity of supported titanium alkoxide catalyst on silica compared to titanium alkoxide in homogeneous catalyst is attributed to higher acidity of the supported $Ti^{+4}$. The catalyst acidity plays an important role for acid catalyzed transesterification and disproportionation reactions in producing aromatic carbonates.

It is possible to prepare a supported metal alkoxide catalyst insitu as an optional method. Reactors are loaded with a treated support. Metal alkoxide solutions are circulated through the reactor at a temperature from ambient to about 400° F. After formation of a supported metal alkoxide catalyst, any remaining solvent is drained off from reactors. After washing the reactors with a suitable solvent such as ethanol, pentane, or toluene and optionally heat treatment of the catalysts in flow of an inert gas such as nitrogen at a temperature from about 80° to about 400° F., preferably from about 100° to about 350° F., the catalysts are ready for the transesterification and disproportionation. For the preparation of supported metal or mixed metal alkoxide catalysts, it is especially important to use a "treated support". An example of a treated support is the treated silica described above. The term "treated support" or "treated silica" is understood to mean a support having an optimized population of surface hydroxyl groups for a given surface area for the preparation of the catalysts described herein.

The present invention herein overcomes the prior problems by decoupling the reaction requirements from the distillation requirements while maintaining the advantageous aspect of high conversion that can be achieved in a reaction-distillation system. An embodiment of the invention is shown in the attached figure which is a simplified flow diagram of the process. The reaction is carried out in a series of fixed bed reactors connected via pumps, heat exchangers, and inlet and outlet pipes to various stages of a multistage distillation column. In the embodiment shown six reactors 20, 30, 40, 50, 60 and 70 are connected to a distillation column 10 containing twenty eight separation stages including the reboiler 80 (stage 28) and partial condenser 90 (stage 1). The reactors all contain beds of the catalyst as described and are connected to stages 11-16 via pipes 105-116 that allow liquid on the respective stages to be circulated through the respective reactors. Reactor operating conditions which are dictated by the reaction kinetic requirements (temperature, pressure and weight hourly space velocity) are independently controlled by heat exchangers and pumps which are not shown. The arrangement allows temperature and pressure conditions to be significantly different from those that exist in the distillation column. Although the draw stream rates can be any value it is preferable that they are comparable to the internal flow rates of the distillation column.

The design and operating conditions (staging above and below the draw stages, reflux ratio, pressure) of the distillation column 10 are dictated by the separation requirements of the reacting system. In this embodiment ten stages are provided above and below the draw stages, the condenser system(condenser 90 and receiver 100) is partial vapor-liquid, with condenser pressure maintained below atmospheric (about 8 psia) and the reflux ratio through flow line 134 is about 7 (total liquid being withdrawn via flow line 132). Ethanol is withdrawn via flow line 133 with the vacuum being maintained through the vapor outlet 135.

Feed phenol in flow line 101, recycle phenol in flow line 102 and feed diethyl carbonate in flow line 103 are combined in flow line 104 and fed to the first draw stage of the column 10. As shown in the material balance contained in TABLE I below, the fresh feed ratio of phenol/diethyl carbonate is about 2:1 as required by the reaction stoichiometry whereas the recycle plus fresh feed stream has a phenol/diethyl carbonate ratio of about 4:1. The presence of excess phenol in the feed stream to the reactor is an important parameter affecting both catalyst performance and reaction selectivity.

Streams 105,111,107,113, 109 and 115 are the column draw streams from stages 11,12,13, 14 and 15 respectively while 106,112,108,114, 110 and 116 are the respective return streams. The conditions listed in the TABLE for each of the streams are at the entrance (after appropriate heat exchangers and pumps) and exit of each of the reactors respectively while the stage temperatures are 239° F., 255° F., 283° F., 309° F., 322° F. and 327° F. The outlet temperature of all of the reactors is maintained at 330° F. by heating the feed via heat exchange (not shown) with an appropriate amount of 165 psi steam. Discharge pressures of the pumps (also not shown) are sufficient to overcome pressure drop through the catalyst beds and fluid heads.

At the above operating conditions of the reactors and column, the overhead liquid product in flow lines 133 is about 98 mol % ethanol and 2 mol % diethyl carbonate (DEC) while the bottoms product in flow line 119 contains about 35 mol % diphenyl carbonate (DPC), 63 mol % phenol and 2 mol % ethyl phenyl carbonate (EPC). Small amounts of diethyl ether, CO2, phenetole and diphenyl ether (DPE) are also produced. A portion of the bottoms is circulated through the reboiler (80) via flow lines 118 and 120.

Diphenyl carbonate is recovered in a separate recovery and purification train which is within the knowledge of those of ordinary skill in the art. Generally the phenol separated from the product is recycled back to the distillation column as noted above.

Since the feed to each reactor is determined by the constitution of the material in the distillation column at the stage where the draw for the reactor is made, the location of the draw will determine whether the reactor is for transesterification or disproportionation. The reactors associated with the upper portion of the distillation column will have feed suitable for transesterification while those associated with the lower portion of the column will be suitable for disproportionation. Conditions are selected to maximize formation of transesterification in some reaction zones, generally toward the upper end of the distillation zone and disproportionation in other reaction zones, generally toward the lower end of the distillation zone. The transesterification reaction may be carried out at 120 to 250° C. and the disproportionation at 120 to 250° C. at pressures sufficient to maintain the reaction mixture in liquid phase and at pressure of at least 50 psi for the transesterification reaction using the catalysts described herein. The distillation column will be operated under conditions of temperature and pressure to obtain a separation of the product diaryl carbonate from the reaction mixture. The actual temperatures will depend on the reactants. For example, the distillation profile in the dimethyl carbonate/phenol system will not be the same as for the diethyl carbonate/phenol system.

A suitable catalyst for use in the present invention in the reactors is a mixed niobium/titanium oxide catalyst supported on treated silica. Granular silica (40.56 g) is treated with a sodium hydroxide solution prepared by dissolving 8.059 NaOH in 226 g water at room temperature for 7 minutes with stirring. The treated silica is washed with cold water thoroughly and then with hot water (about 65° C.) several times to remove trace of sodium on silica. The treated silica is dried at 150° C. for 2 hours and then calcined at 325° C. for 2 hours. This calcined silica contains 300 ppm Na by weight. A niobium alkoxide solution was prepared by dissolving 0.844 g of $Nb(OC_4H_{9-n})_5$ in 80 ml toluene. 8.46 g of the treated silica is refluxed in the above niobium butoxide solution for 3 hours in a flask with water-cooled condenser. After cooling, the excess solution in the flask is drained out of the flask. A water-methanol mixture is prepared by mixing 0.645 g water with 90 ml methanol. This water-methanol mixture is poured into the flask and the content in the flask again refluxed. After an hour reflux, the excess solution in the flask is drained out. A titanium tetrabutoxide solution prepared by dissolving 3.67 g of titanium butoxide in 80 ml toluene is poured into the flask and then the content in the flask refluxed for 1 hour 45 minutes. The excess toluene in the flask is distilled off from the flask. The material in the flask is recovered from the flask and dried at 120° C. in a vacuum oven for 1 hour. The dried silica is calcined at 500° C. for to 2 hours.

TABLE

|  | 101 | 102 | 103 | 104 | 105 | 106 | 107 | 108 | 109 |
|---|---|---|---|---|---|---|---|---|---|
| Temperature F. | 347 | 200 | 200 | 256 | 344 | 330 | 340 | 330 | 335 |
| Pressure psi | 20 | 15 | 30 | 15 | 48.0 | 50.0 | 48.0 | 50.0 | 48 |
| Mole Flow lbmol/hr | 189.5 | 212.0 | 109.2 | 510.7 | 1116.2 | 1116.2 | 1025.7 | 1025.7 | 932.9 |
| Mass Flow (total) lb/hr | 18169 | 19952 | 12900 | 51021 | 120000 | 120001 | 1 10000 | 110000 | 100000 |
| Mass Flow (vapor) lb/hr |  |  |  |  |  |  |  |  |  |
| Mass Flow (liquid) lb/hr | 18169 | 19952 | 12900 | 51021 | 120000 | 120001 | 1 10000 | 1 10000 | 100000 |
| Volume Flow(total)cufUhr | 307 | 314 | 232 | 866 | 1920 | 1862 | 1714 | 1682 | 1538 |
| Volume Flow (vapor) cu |  |  |  |  |  |  |  |  |  |
| Volume Flow(liquid)culVhr | 307 | 314 | 232 | 866 | 1920 | 1862 | 1714 | 1682 | 1538 |
| Enthalpy M MBtu/hr | −10.9 | −12.9 | −31.4 | −55.4 | −89.4 | −89.7 | −69.5 | −69.7 | −59.7 |
| Mole Flow lbmol/hr |  |  |  |  |  |  |  |  |  |
| PHENOL | 184.61 | 212.00 | 0.00 | 396.61 | 848.35 | 811.38 | 837.16 | 816.98 | 782.71 |
| DEC | 0.00 | 0.00 | 109.20 | 109.20 | 85.00 | 69.22 | 22.91 | 15.83 | 5.81 |
| EPC | 4.61 | 0.00 | 0.00 | 4.61 | 23.52 | 18.12 | 14.57 | 8.55 | 9.28 |
| DPC | 0.00 | 0.00 | 0.00 | 0.00 | 79.82 | 101.01 | 85.24 | 98.34 | 82.89 |
| PHENETOL | 0.24 | 0.00 | 0.00 | 0.24 | 71.56 | 71.56 | 62.81 | 62.81 | 50.48 |
| ETHANOL | 0.00 | 0.00 | 0.00 | 0.00 | 7.94 | 44.91 | 2.90 | 23.08 | 0.83 |
| DPE | 0.000 | 0.000 | 0.000 | 0.000 | 0.011 | 0.011 | 0.104 | 0.104 | 0.872 |
| CO2 | 0.000 | 0.000 | 0.000 | 0.000 | 0.001 | 0.001 | 0.001 | 0.001 | 0.000 |
| DEE | 0.000 | 0.000 | 0.000 | 0.000 | 0 | 0 | 0 | 0 | 0.000 |
| Mole Frac |  |  |  |  |  |  |  |  |  |
| PHENOL | 0.974 | 1 | 0 | 0.974 | 0.76 | 0.727 | 0.816 | 0.797 | 0.839 |
| DEC | 0 | 0 | 1 | 1 | 0.076 | 0.062 | 0.022 | 0.015 | 0.006 |
| EPC | 0.024 | 0 | 0 | 0.024 | 0.021 | 0.016 | 0.014 | 0.008 | 0.01 |
| DPC | 0 | 0 | 0 | 0 | 0.072 | 0.09 | 0.083 | 0.096 | 0.089 |
| PHENETOL | 0.001 | 0 | 0 | 0.001 | 0.064 | 0.064 | 0.061 | 0.061 | 0.054 |
| ETHANOL | 0 | 0 | 0 | 0 | 0.007 | 0.04 | 0.003 | 0.023 | 0.001 |
| DPE | 0 | 0 | 0 | 0 | 0 | 0 | 0 | 0 | 0 |
| CO2 | 0 | 0 | 0 | 0 | 0 | 0 | 0 | 0 | 0.001 |
| DEE | 0 | 0 | 0 | 0 | 0 | 0 | 0 | 0 | 0 |

|  | 110 | 111 | 112 | 113 | 114 | 115 | 116 | 119 | 133 |
|---|---|---|---|---|---|---|---|---|---|
| Temperature F. | 330 | 340 | 330 | 347 | 330 | 354 | 330 | 355 | 114 |
| Pressure psi | 50 | 48.0 | 50.0 | 48.0 | 50.0 | 48.0 | 50.0 | 9 | 8 |
| Mole Flow lbmol/hr | 933.9 | 1265.8 | 1266.3 | 1186.5 | 1187.5 | 1108.8 | 1108.8 | 299.2 | 213.7 |
| Mass Flow (total) lb/hr | 100000 | 140000 | 140000 | 130000 | 130000 | 120000 | 120000 | 41 108 | 10050 |
| Mass Flow (vapor) lb/hr |  |  |  |  |  |  |  |  |  |
| Mass Flow (liquid) lb/hr | 100000 | 140000 | 140000 | 130000 | 130000 | 120000 | 120000 | 41 108 | 10050 |
| Volume Flow(total)cufUhr | 1525 | 2671 | 2588 | 2353 | 2262 | 2033 | 1943 | 441 | 206 |
| Volume Flow (vapor) cu |  |  |  |  |  |  |  |  |  |
| Volume Flow(liquid)culVhr | 1525 | 2671 | 2588 | 2354 | 2262 | 2033 | 1943 | 441 | 206 |
| Enthalpy M MBtu/hr | −59.8 | −254.9 | −255.1 | −190.7 | −191.3 | −123.0 | −123.9 | −24.8 | −25.8 |
| Mole Flow lbmol/hr |  |  |  |  |  |  |  |  |  |
| PHENOL | 772.60 | 375.97 | 329.50 | 527.93 | 478.67 | 703.07 | 654.85 | 188.31 | 0.00 |
| DEC | 3.47 | 802.80 | 772.87 | 526.69 | 498.98 | 240.43 | 216.78 | 0.00 | 2.71 |
| EPC | 3.84 | 20.21 | 32.61 | 29.41 | 34.57 | 29.71 | 28.80 | 4.64 | 0.00 |
| DPC | 89.66 | 12.23 | 29.27 | 32.44 | 53.99 | 56.87 | 81.44 | 104.20 | 0.00 |
| PHENETOL | 50.48 | 16.90 | 16.90 | 39.86 | 40.86 | 61.52 | 61.52 | 1.01 | 0.00 |
| ETHANOL | 10.94 | 37.69 | 84.16 | 30.17 | 79.43 | 17.22 | 65.44 | 0.00 | 209.85 |
| DPE | 1.872 | 0 | 0 | 0 | 0 | 0.001 | 0.001 | 1.000 | 0.000 |
| CO2 | 1.000 | 0.003 | 0.503 | 0.002 | 1.002 | 0.002 | 0.002 | 0.000 | 0.668 |
| DEE | 0.000 | 0.005 | 0.505 | 0 | 0 | 0 | 0 | 0.000 | 0.444 |

TABLE-continued

| | Mole Frac | | | | | | | | |
|---|---|---|---|---|---|---|---|---|---|
| PHENOL | 0.827 | 0.297 | 0.26 | 0.445 | 0.403 | 0.634 | 0.591 | 0.629 | 0 |
| DEC | 0.004 | 0.634 | 0.61 | 0.444 | 0.42 | 0.217 | 0.196 | 0 | 0.013 |
| EPC | 0.004 | 0.016 | 0.026 | 0.025 | 0.029 | 0.027 | 0.026 | 0.016 | 0 |
| DPC | 0.096 | 0.01 | 0.023 | 0.027 | 0.045 | 0.051 | 0.073 | 0.348 | 0 |
| PHENETOL | 0.054 | 0.013 | 0.013 | 0.034 | 0.034 | 0.055 | 0.055 | 0.003 | 0 |
| ETHANOL | 0.012 | 0.03 | 0.066 | 0.025 | 0.067 | 0.016 | 0.059 | 0 | 0.982 |
| DPE | 0 | 0 | 0 | 0 | 0 | 0 | 0 | 0 | 0 |
| CO2 | 0.002 | 0 | 0 | 0 | 0.001 | 0 | 0 | 0.003 | 0 |
| DEE | 0.001 | 0 | 0 | 0 | 0 | 0 | 0 | 0 | 0.003 |

The invention claimed is:

1. A process for the production of diaryl carbonate comprising the steps of feeding aromatic hydroxy and dialkyl carbonate to a distillation zone having a plurality of stages, withdrawing liquid comprising aromatic hydroxy and dialkyl carbonate from a first distillation stage to a first reaction zone to contact the liquid with a transesterification catalyst under conditions conducive to transesterification, returning a product from the first reaction zone to the distillation zone, withdrawing liquid comprising aryl alkyl carbonate from a second distillation stage which is positioned below said first distillation stage to a second reaction zone to contact the liquid with a disproportation catalyst under conditions conducive to disproportation, returning a product from the second reaction zone to the distillation zone, and separating diaryl carbonate as bottoms and alkyl alcohol as overheads.

2. The process according to claim 1 wherein each of the reaction zones is operated at conditions independent of the distillation zone.

3. The process according to claim 1 wherein the distillation zone includes separation zones positioned above and below the distillation stages from which the liquid is withdrawn and said aromatic hydroxy and dialkyl carbonate are fed to the top most distillation stage from which liquid is withdrawn.

4. The process according to claim 1 wherein the aromatic hydroxy is phenol and the dialkyl carbonate diethyl carbonate.

5. The process according to claim 4 wherein the ratio of phenol to diethyl carbonate in the feed is about 2:1 and the total ratio of phenol to diethyl carbonate is about 4:1.

6. A process of the production of diaryl carbonate comprising:
    (a) distillation zone having an upper end, a lower end and a plurality of distillation stages arrayed along said distillation zone;
    (b) a plurality of reaction zones arrayed along said distillation zone and associated with different distillation stages;
    (c) supplying dialkyl carbonate and an aromatic hydroxy compound to said distillation zone;
    (c) withdrawing a stream comprising dialkyl carbonate and an aromatic hydroxy compound from a first distillation stage to a first reaction zone;
    (d) maintaining said first reaction zone under reaction conditions conducive for the transesterification of dialkyl carbonate and an aromatic hydroxy compound to produce alkyl aryl carbonate;
    (e) transesterifing the dialkyl carbonate with the aromatic hydroxy compound in the presence of a catalyst to form alkyl aryl carbonate;
    (f) returning a product stream from said first reaction zone to said distillation zone;
    (g) withdrawing a stream comprising alkyl aryl carbonate and an aromatic hydroxy compound from a second distillation stage to a second reaction zone;
    (h) maintaining the second reaction zone under reaction conditions conducive for the disproportionation of alkyl aryl carbonate to dialkyl carbonate;
    (i) disproportionating the alkyl aryl carbonate in the presence of a catalyst to produce diaryl carbonate;
    (j) returning a product stream from said secondary reaction zone to said distillation zone;
    (k) removing vaporous alkyl alcohol and liquid diaryl carbonate from the distillation zone.

7. The process according to claim 6 comprising successive distillation stages and successive reaction zones associated with said distillation stages between the upper end and the bottom end of the distillation zone.

8. The process according to claim 7 comprising a plurality of first reaction zones and a plurality of second reaction zones.

9. The process according to claim 6 wherein the dialkyl carbonate comprises diethyl carbonate and an aromatic hydroxy compound comprises phenol.

10. The process according to claim 6 wherein said transesterification catalyst is solid catalyst composition selected from the group consisting of oxides, hydroxides, oxyhydroxides or alkoxides of two to four elements from Group IV, V and VI of the Periodic Table supported on porous material which have surface hydroxyl groups.

11. The process according to claim 6 wherein said disproportionation catalyst is a solid catalyst composition selected from the group consisting of oxides, hydroxides, oxyhydroxides or alkoxides of two to four elements from Group IV, V and VI of the Periodic Table supported on porous material which have surface hydroxyl groups.

12. The process according to claim 6 wherein said primary reaction zone is toward the upper end of said reaction zone.

13. The process according to claim 6 wherein said secondary reaction zone is toward the lower end of said reaction zone.

* * * * *